United States Patent [19]

Yoshimura et al.

[11] Patent Number: 4,797,477

[45] Date of Patent: Jan. 10, 1989

[54] PROCESS FOR PREPARING SIALIC ACID DERIVATIVES

[75] Inventors: Shoji Yoshimura, Iruma; Yoichiro Tani; Youzi Matsuzaki, both of Tokorozawa; Masayoshi Ito, Kunitachi; Yoshiyasu Shitori, Tokyo; Tomoya Ogawa, Musashino, all of Japan

[73] Assignee: Mect Corporation, Tokyo, Japan

[21] Appl. No.: 84,018

[22] Filed: Aug. 11, 1987

[30] Foreign Application Priority Data

Aug. 12, 1986 [JP] Japan .................................. 61-189340

[51] Int. Cl.[4] .......................... C07H 5/06; C07H 15/04
[52] U.S. Cl. ..................................... 536/18.5; 536/4.1; 536/17.2; 536/18.2; 536/18.4; 536/18.7; 536/53; 536/55.3; 536/124
[58] Field of Search ....................... 536/4.1, 17.2, 18.2, 536/18.4, 18.5, 18.7, 55.3, 53, 124

[56] References Cited

U.S. PATENT DOCUMENTS 3,950,322  4/1976  Thomas et al. .................. 536/53
4,694,076  9/1987  Ogawa et al. ................... 536/4.1

FOREIGN PATENT DOCUMENTS 57-106691  7/1982  Japan ............................... 536/18.2
57-106692  7/1982  Japan ............................... 536/18.2
58-055495  4/1983  Japan ............................... 536/4.1

OTHER PUBLICATIONS

Bernthsen; *Text Book of Organic Chemistry;* 1932, pp. 178–185.
Noller; *Chemistry of Organic Compounds* 2nd Edition; 1957, pp. 165–174.

*Primary Examiner*—Ronald W. Griffin
*Assistant Examiner*—Nancy S. Carson
*Attorney, Agent, or Firm*—Oblon, Fisher, Spivak, McClelland & Maier

[57] ABSTRACT

The present invention relates to a new process for preparing 3-O-(sodium(5-acetamide-3,5-dideoxy-alpha-D-glycero-D-galacto-2-noneuro pyranosyl)onate-1,2-di-O-tetradecyl-Sn-glycerol (3).

7 Claims, No Drawings

PROCESS FOR PREPARING SIALIC ACID DERIVATIVES

BACKGROUND OF THE INVENTION

1. Field of the Invention

The present invention relates to a novel process for preparing sialic acid derivatives. More particularly, it relates to the process for preparing 3-O-(sodium(5-acetamide-3,5-dideoxy-alpha-D-glycero-D-galacto-2-noneuro pyranosyl)onate-1,2-di-O-tetradecyl-Sn-glycerol (3).

2. Description of the Related Prior Art

Sialic acid is known to be present as a sialo complex (glycoprotein, glycolipid, oligosaccharide and polysaccharide) on the surfaces of cells of animals and of certain bacteria.

This compound has drawn attention as a singular active molecule that is related to nerve function, cancer, inflammation, immunity, virus infection, differentiation, hormone receptor and the like and is present locally on the surfaces of cells. However, there is no established theory yet as to the role said sialic acid plays in a sialo complex.

It is disclosed in a publication (refer to Laid-Open patent application No. 164798/1984: U.S. Ser. No. 680,498) that various derivatives can be obtained by introducing said sialic acid into a sugar-donor by a known method while introducing a sugar-receptor by a known method, then reacting these two. The method is shown by the following formula:

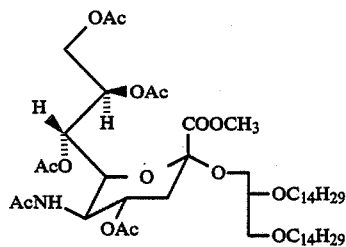

(1)

↓

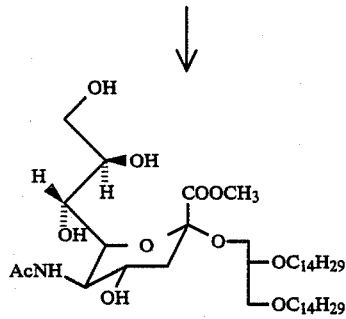

(2)

According to the method, Compound (1) is first dissolved in methanol, to which $NaOCH_3$ is added and the mixture is agitated at room temperature for one hour. Subsequently the reaction liquor is neutralized by use of cation exchanger (Amberlist A-15) and is then filtered and concentrated under reduced pressure, whereby Compound (2) is obtained as a crystal. (Yield, 67%).

But in the above invention the objective Compound (3) is not disclosed. In other words, the method for preparing Compound (3) directly from Compound (1) is not known. Therefore, said Compound (3) has to be obtained through Compound (2). (Refer to the following formula.)

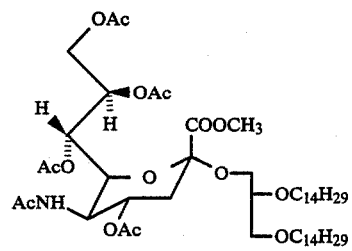

(1)

$NaOCH_3$ (+MeOH)
Dowex · 50W × 8 (cation exchanger)
Column Purification

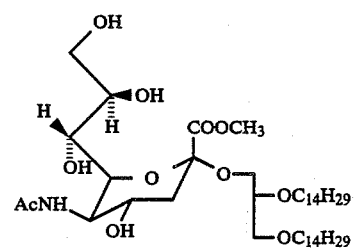

(2)

1 NNaOH (+THF)
Amberlite IRC-50 (cation exchanger)
Freeze-Drying

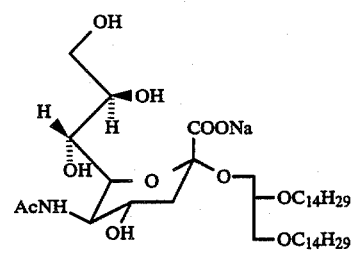

(3)

On the other hand, it is suggested therein that the compound obtained according to the above method is effective as a remedy for nerve troubles.

OBJECT OF THE PRESENT INVENTION

The object of the present invention relates to the process for preparing sialic acid derivatives effective as a remedy for nerve troubles in a single stage. Another object of the present invention is to provide a process for preparation of the derivatives with a very high yield.

SUMMARY OF THE INVENTION

In order to accomplish the above objects, the present invention is constituted as follows. That is to say, the present invention prepares the compound represented by the formula:

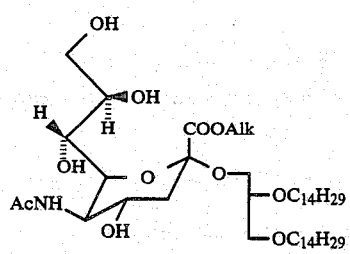

(3)

wherein Ac stands for an acetyl group and Alk is an alkali metal, characterized by hydrolyzing in an ROH aqueous solution of an alkali metal hydroxide the compound represented by the general formula:

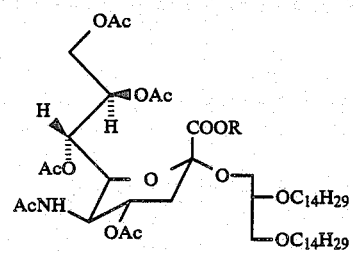

(1)

wherein Ac is the same as defined above and R stands for a lower alkyl group having 1 to 5 carbon atoms.

Hereinafter we explain the present invention further in detail.

An outline of the process in accordance with the present invention is shown by the following reaction formulae.

Reaction Formula I

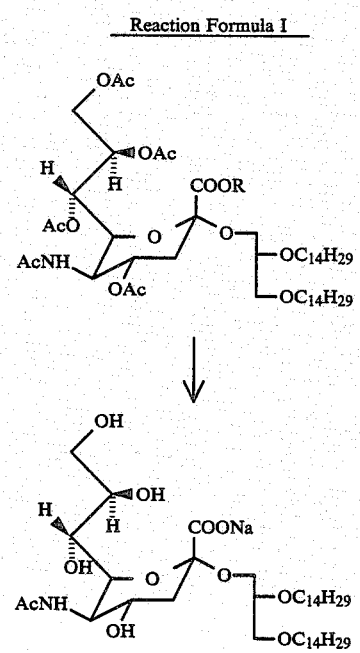

To begin with, said Compound (1) to be used in the present invention can be obtained by, for example, the reaction between Compound (4) and 1,2-di-O-tetradecyl-Sn-glycerol (5). (Refer to the following formula.)

Reaction Formula II

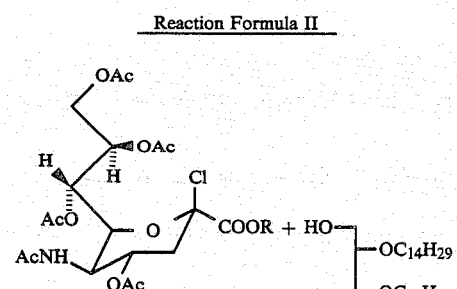

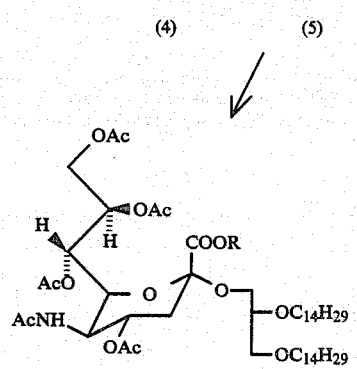

(1)

In the Reaction Formula I, Compound (1) is dissolved in a solvent such as methanol, ethanol or THF, then a 0.5–2N aqueous solution of sodium hydroxide is added thereto and the mixture is agitated at 10°–30° C. for ten hours. Said sodium hydroxide is used in an amount of 3–10 moles relative to 1 mole of Compound (1). In this instance, methanol can be advantageously used as the solvent. On the other hand, it is preferable that the aqueous solution of sodium hydroxide has a concentration of 1–1.5N.

The reaction product thus obtained is isolated and purified by an ordinary method such as column chromatography.

When the column chromatography is performed, it is preferable to use the reaction liquor after it has been neutralized with cation exchanger (for example, Amberlite IRC-50).

Further, in the present invention a mixture of Compound (1) (called "alpha-body") and Compound (6) (called "beta-body") that is known as an isomer thereof can be used as the material.

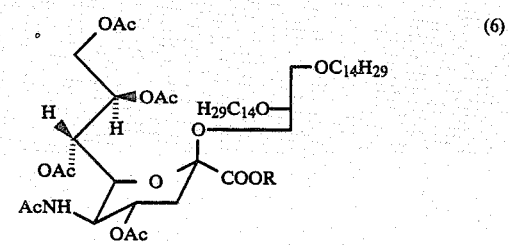

(6)

In this instance it is preferable that in the column chromatography to be used for isolation and purification of Compound (3) and Compound (7), there be used

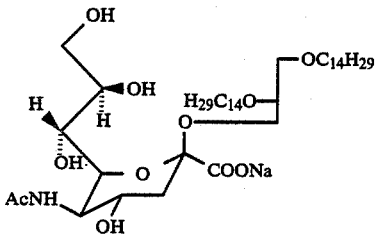

(7)

silica gel as the carrier, the most preferable being $C_{18}$-silica gel.

EFFECTS OF THE PRESENT INVENTION (1) Compound (3) can be prepared from Compound (1) in a single stage. Accordingly, the object product can be prepared efficiently.
(2) Since the production yield is high, the cost of preparation becomes low.
(3) Compound (3) has high purity. This is due to the fact that purification is effected by using $C_{18}$-silica gel. Said $C_{18}$-silica gel can be regenerated and used repeatedly which leads to the reduction of cost. (In this connection, according to the conventional method such regeneration and repeated use of silica gel was impossible.)
(4) The desired Compound (3) can be obtained with a high yield and efficiently, even from a mixture of Compound (1) and Compound (6).

EXAMPLES

Hereinafter we explain the present invention by concrete Examples. These Examples are shown only for the purpose of explanation of the invention and the present invention is by no means limited by them.

REFERENTIAL EXAMPLE 1

Process for Preparing Compound (1)

(3-O-(methyl(5-acetamide-4,7,8,9-tetra-O-acetyl-3,5-dideoxy-alpha-D-glycero-D-galacto-2-noneuro pyranosyl)onate)-1,2-di-O-tetradecyl-Sn-glycerol)

In 2.5 l of anhydrous tetrahydrofuran, 106.8 g (0.22 mol) of 1,2-di-O-tetradecyl-Sn-glycerol (5) was dissolved, and subsequently 155 g of molecular sieve 4A powder was added thereto and the mixture was agitated at room temperature for one hour. Shielding from light with aluminum foil, 95 g (0.372 mol) of trifluoromethane silver sulfonate was added thereto while cooling it to $-5°$ C., and thirty minutes later an anhydrous tetrahydrofuran-one-liter-solution of methyl 2-chloro-4,7,8,9-tetra-O-acetyl-beta-D-N-acetylneuraminate (4) (0.18 mol) was added thereto. Twenty minutes later, an anhydrous tetrahydrofuran-200 ml-solution of 35.2 g (0.186 mol) of anhydrous stannous chloride was trickled down for a period of one hour. Under the temperature $-5°$ C., the mixture was agitated for three hours, then agitated at room temperature for eight hours. After completion of the reaction, the reaction liquor was filtered and the residue was washed with ether, and the solution thus obtained was concentrated to one liter, whereafter four liters of ether was added thereto. It was then neutralized with a saturated solution of sodium carbonate, and the deposits were filtered and the residue was washed with ether; the solution obtained thereby was dried by means of anhydrous magnesium sulfate.

The solvent was distilled off, and 240 g of crude product was obtained.

The crude product thus obtained was subjected to purification by means of silica gel column chromatography (Wacogel C-200 1.8 kg, Developing solvent, toluene:ethyl acetate=2:1), thereby 115 g of the first purified material was obtained. The thus obtained product was subjected again to silica gel column chromatography purification (6 kg silica gel (C-300), Developing solvent, toluene:ethyl acetate=1:1, atmospheric pressure 3) and thereby 66 g of the pure product of Compound (1) was obtained, (Yield 37%). Also 18 g of the pure product of Compound (6) was obtained thereby, (Yield 10%).

Physical Properties of Compound (1)

Elemental Analysis: $C_{51}H_{91}NO_{15}$: Calculated Values: C: 63.92H: 9.47N: 1.46. Measured Values: C: 63.83H: 9.50N: 1.43.

$^1$H-NMR$_{400}$ MHz$^{ppm}$ (CDCl$_3$, TMS): 1.972 (1H, t, J=12.6 Hz, H$_{3ax}$), 1.879 (3H, s, CH$_3$CONH—), 2.601 (3H, dd, J=4.6, 12.6 Hz, H$_{3eq}$).

REFERENTIAL EXAMPLE 2

Physical Properties of Compound (6)

(3-O-(methyl(5-acetamide-4,7,8,9-tetra-O-acetyl-3,5-dideoxy-beta-D-glycero-D-galacto-2-noneuro pyranosyl)onate)-1,2-di-O-tetradecyl-Sn-glycerol)

Elemental Analysis: $C_{51}H_{91}NO_{15}$: Calculated Values: C: 63.92, H: 9.47, N: 1.46. Measured Values: C: 63.75, H: 9.61, N: 1.45.

$^1$H-NMR$_{400}$ MHz$^{ppm}$ (CDCl$_3$TMS): 1.697 (1H, t, J=12.9 Hz, H$_{3ax}$), 1.879 (3H, s, CH$_3$CONH—), 2.451 (1H, dd, J=4.9, 12.9 Hz, H$_{3eq}$).

EXAMPLE 1

Process for Preparation of Compound (3)

(3-O-(sodium(5-acetamide-3,5-dideoxy-alpha-D-glycero-D-galacto-2-noneuro pyranosyl)onate)-1,2-di-O-tetradecyl-Sn-glycerol)

In 1 ml of methanol, 236 mg of Compound (1) was dissolved, whereafter 1.5 ml of an aqueous solution of 1N-sodium hydroxide was added thereto and the mixture was agitated at room temperature for six hours. After the reaction pH was adjusted to pH=7 with 50 ml of Amberlite IRC, the mixture was adsorbed on a column filled with 40 ml of YMC-GEL, ODS (60 Å, 60/200 mesh, Yamamura Kagaku Kenkyusho). After sodium acetate was melted out with 500 ml of water, methanol was distilled off from the fraction melted out with 500 ml of methanol, and the residue, with addition of water, was subjected to freeze-drying, and subsequently subjected to vacuum-drying; whereby 192.4 mg of colorless powder, Compound (3), was obtained, (Yield 97.9%).

Physical Properties of Compound (3)

Decomposing Point: 216°-218° C.

Elemental Analysis: $C_{42}H_{80}NO_{11}Na.2H_2O$: Calculated Values: C: 60.48, H: 10.15, N: 1.71. Measured Values: C: 60.33, H: 9.75, N: 1.70.

TLC Rf=0.40 (TLC Plate RP-18$_{254s}$: Developing solvent, methanol).

IR$\nu_{max}^{KBr}$ Cm$^{-1}$: 1620 (—C00°) 1110.

$^1$H-NMR$_{400}$ MHz$^{ppm}$ (DMSO-d$_6$, TMS): 1.868 (3H, s, CH$_3$CONH—), 2.620 (1H, dd, J=11.0, 4.6 Hz, H$_{3eq}$).

COMPARATIVE EXAMPLE 1

Process for Preparation of Compound (2)

(3-O-(methyl(5-acetamide-3,5-dideoxy-alpha-D-glycero-D-galacto-2-noneuro pyranosyl)onate)-1,2-di-O-tetradecyl-Sn-glycerol)

In 1 ml of methanol, 973 mg of Compound (1) was dissolved, whereafter 0.7 mol times the sodium metal was added thereto, and after agitation for forty minutes, the mixture was neutralized with cation exchanger (Dowex 50WX8), and the solvent was distilled off from the thus obtained filtrate under reduced pressure; whereby Compound (2) was obtained. Amount prepared 733 mg, Yield 90.9%.

Physical Properties of Compound (2)

Melting point: 106°–109° C.
Elemental Analysis: $C_{43}H_{83}NO_{11}.2.5H_2O$ MW=835.17. Calculated Values: C: 61.84, H: 10.06, N: 1.67. Measured Values: C: 62.07, H: 10.17, N: 1.27.
$^1$H-NMR$_{400}$ MHz$^{ppm}$ (CDCl$_3$, TMS): 1.900 (1H, t, J=13.0 Hz, H$_{3ax}$), 2.066 (3H, s, —NHCOC$\underline{H}_3$), 2.798 (1H, dd, J=4.6, 130 Hz, H$_{3eq}$), 3.830 (3H, s, —COOCH$_3$).
IR$\nu_{max}^{KBr}$ Cm$^{-1}$: 1720 (—COOCH$_3$), 1640, 1570.

COMPARATIVE EXAMPLE 2

Process for Preparation of Compound (3)

(3-O-(sodium(5-acetamide-3,5-dideoxy-alpha-D-glycero-D-galacto-2-noneuro pyranosyl)Onate)-1,2-di-O-tetradecyl-Sn-glycerol)

To 147 mg of Compound (2), 6 ml of 1N NaOH and 0.5 ml of THF were added and after agitation for two hours the mixture was neutralized with Amberlite IRC-50, and filtered. The filtrate was subjected to freeze-drying, whereby 139 mg of colorless, amorphous crystals, Compound (3), was obtained. Yield 93.66%.

Physical Properties of Compound (3)

Decomposing Point: 185°–195° C.
Elemental Analysis: $C_{42}H_{80}NO_{11}Na.2H_2O$: Calculated Values: C: 60.48, H: 10.15, N: 1.71. Measured Values: C: 60.36, H: 9.72, N: 1.71.
$^1$H-NMR$_{400}$ MHz$^{ppm}$ (DMSO-d$_6$, TMS): 1.868 (3H, s, C$\underline{H}_3$CONH—), 2.620 (1H, dd, J=11.0, 4.6 Hz, H$_{3eq}$).
IR$\nu_{max}^{KBr}$ Cm$^{-1}$: 1620 (—COO$^\ominus$), 1110.

What is claimed is:

1. A process for preparing a compound represented by the formula:

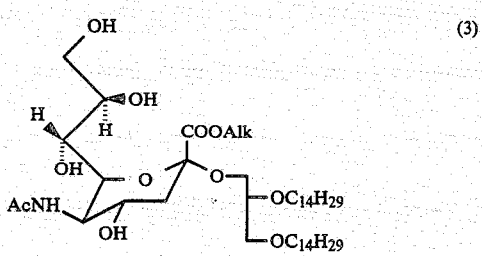

wherein Ac is acetyl and Alk is an alkali metal, consisting essentially of:
   hydrolyzing, in a single step, a compound of the formula:

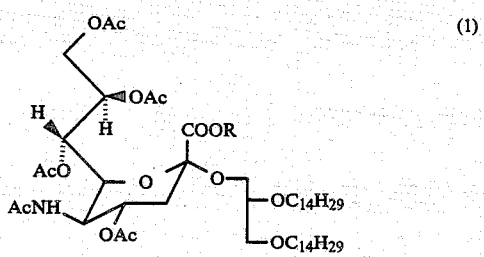

wherein Ac is as defined above and R is $C_{1-5}$ alkyl, in an aqueous ROH solution of an alkali metal hydroxide.

2. The process as described in claim 1, wherein the ROH is methanol.

3. The process as described in claim 1, wherein the alkali metal hydroxide is sodium hydroxide.

4. The process as described in claim 3, wherein a concentration of the aqueous sodium hydroxide solution is from 0.5-2N.

5. The process as described in claim 3, wherein the sodium hydroxide is used in an amount of 3-10 moles to 1 mole of the compound 1.

6. The process as described in claim 1, wherein the compound (1) is dissolved in a lower aliphatic alcohol or THF solvent before hydrolyzing.

7. The process as described in claim 4, wherein the solvent is methanol.

* * * * *